United States Patent [19]

Schulte

[11] Patent Number: 4,708,873

[45] Date of Patent: Nov. 24, 1987

[54] METHOD OF CHEMICALLY DEBRIDING UNCERATED NECROTIC TISSUE

[76] Inventor: Thomas L. Schulte, 218 Family Farm Dr., Woodside, Calif. 94062

[21] Appl. No.: 823,852

[22] Filed: Jan. 29, 1986

[51] Int. Cl.⁴ .................... A61K 35/78; A61K 31/615
[52] U.S. Cl. ................................ 424/195.1; 514/166;
514/947
[58] Field of Search ..................... 424/195.1; 514/166,
514/947

[56] References Cited

U.S. PATENT DOCUMENTS 4,497,824  2/1985  Schulte ............................... 514/166

OTHER PUBLICATIONS

Lewis Med. Botany, p. 336, 1977.
The Merck Index, 10th ed. 1983, p. 46.
Taber's Cyclopedic Medical Dictionary 17th ed., p. A-59.
International Dictionary of Medicine and Biology, vol. 1, p. 82, 1986.

*Primary Examiner*—J. R. Brown
*Assistant Examiner*—John W. Rollins, Jr.
*Attorney, Agent, or Firm*—Millen & White

[57] ABSTRACT

Debridement of ulcerated necrotic tissue of the skin or mucous membrane is promoted by applying thereto an aqueous solution of biphenamine and aloe vera, the former preferably being dissolved in the latter, thereby promoting healing of the lesion.

11 Claims, No Drawings

METHOD OF CHEMICALLY DEBRIDING UNCERATED NECROTIC TISSUE

BACKGROUND OF THE INVENTION

This invention relates to a method for chemically debriding abnormal, damaged or necrotic tissue which is related to that claimed in my U.S. Pat. No. 4,497,824, whose disclosure is incorporated herein by reference.

The treatment topically of traumatized or pathological areas of the body having abnormal ischemic tissue around or covering a lesion is often hampered by the fact that the ischemic tissue presented by the affected area provides a pathological surface which is an effective barrier between normal tissue and the natural healing process or a healing agent employed to thereby initiate the healing process. In such cases, physicians sometimes resort to the very painful task of manually debriding the abnormal tissue or covering the area with bandages soaked in medication to prevent infection while keeping the surface moist. Both of these approaches have obvious limitations and pose well known problems.

There therefore is a long-standing need for an effective chemical debriding agent. There is also a need for a non-toxic, non-allergenic bacteriostat and fungistat which is also effective in promoting the normal healing of traumatized or pathological epithelium by suppressing infection and/or the natural inflammatory process.

The compositions employed in the method claimed in U.S. Pat. No. 4,497,824 comprise biphenamine ( -diethylaminoethyl 3-phenyl-2-hydroxybenzoate) base or pharmaceutically acceptable acid addition salt thereof. Salts of this compound are known to have a variety of activities, including local anesthetic (U.S. Pat. No. 1,976,922); treatment of seborrhea capitis in a shampoo (U.S. Pat. No. 3,123,531); as well as antihistaminic and bactericidal activity and fungicidal properties (U.S. Pat. No. 2,594,350; Report Annual Meeting So. Med. Assoc., Nov. 6, 1961).

Biphenamine hydrochloride has been sold as a 1% ointment, under the trademark "Melsaphine", as a topical anesthetic agent possessing bactericidal, fungicidal and antihistamine properties and as a 1% aqueous shampoo under the trademark "Alvinine", Federal Register, Vol. 34, No. 189, page 153, Oct. 2, 1969. See also U.S. Pat. No. 3,123,531.

Although its use in a shampoo for treating seborrhea and related conditions is claimed in U.S. Pat. No. 3,123,531, nothing was known concerning its ability to promote the healing of traumatized or pathological epithelium.

The method of this invention also employs aloe vera. (As used herein, the term aloe vera means the viscous, sticky juice of the aloe vera plant.) Although aloe vera does not itself debride, it stimulates wound healing and inhibits the formation of granulation tissue.

The juice from the aloe vera plant has been used as a home remedy for minor burns to reduce the pain and the inflammation associated therewith. The use of biphenamine and aloe vera in combination has proved to be especially effective in debriding and stimulating wound healing.

The topical compositions employed in the method of this invention optionally also comprise, especially when the lesion is epithelial, an amount of a skin penetrant, e.g., DMSO (dimethyl sulfoxide) or propylene glycol, which by itself has no debriding or wound healing enhancement effects, at least in the amount employed. U.S. Pat. Nos. 3,551,554 and 3,711,602 disclose that DMSO is effective as an agent for enhancing tissue penetration of physiologically active agents. U.S. Pat. No. 3,549,770 discloses (Example 36) the topical application of a mixture of acetylsalicyclic acid and DMSO is more effective than DMSO alone to relieve the pain and muscle spasm of rheumatoid spondylitis. See also U.S. Pat. Nos. 3,711,602; 3,711,606; and 3,743,727 and references cited therein. These patents disclose that the tissue penetration of physiologically active compounds, inter alia, steroidal agents and certain antimicrobial agents, can be enhanced by DMSO. U.S. Pat. No. 3,740,420 discloses DMSO compositions for topical administration containing thickening agents.

SUMMARY OF THE INVENTION

In a method of use aspect, this invention relates to a method for promoting the healing of an abnormal, ulcerated necrotic tissue on skin or mucous membrane of a patient which comprises applying topically to the affected area of the patient an amount of biphenamine, as an aqueous mixture comprising a pharmaceutically acceptable carrier, effective to promote debridement of necrotic tissue from the affected area, thereby promoting the healing of the affected area, and also applying to the affected area an amount of aloe vera effective to further promote wound healing. The biphenamine is preferably applied in admixture with the aloe vera, most preferably as a solution therein.

DETAILED DISCUSSION

The aqueous mixture of biphenamine (base or acid addition salt thereof) and optional skin penetrant and the aloe vera are applied topically to the ulcerated area of the skin or mucous membrane, e.g., of the mouth, throat, nasal passages, ear canals and drums, anal or vaginal regions, bladder or urethra. They are applied as a solution in an aqueous pharmaceutically acceptable carrier or diluent for the biphenamine, which preferably is the aloe vera. The mixture preferably is liquid, e.g., in the form of clear solutions, such as drops, aerosols or sprays, or in the form of lotions, or other viscous aqueous liquids. The mixture can also be semi-solid or solid, e.g., in the form of an ointment or creas. Viscosity regulating agents in addition to the aloe vera, such as thickeners and gelling agents, e.g., glycerin, sodium carboxymethyl-cellulose, etc., can also be used to regulate flowability. See U.S. Pat. Nos. 3,740,420 and 3,711,602, whose disclosures are incorporated herein by reference. Propylene glycol itself is useful as a viscosity raising agent. They can be in the form of an oil-in-water or water-in-oil emulsion, as disclosed in U.S. Pat. No. 3,740,420, or as a single phase aqueous solution, the latter being preferred. Organic solvents, e.g., ethanol or isopropanol, can also be present.

Although the biphenamine can be present in the aqueous mixture employed, which preferably is the aloe vera, at any convenient concentration, generally concentrations of up to 1% by weight, e.g., from about 0.1% to 1%, are employed except for instillations, where lower concentrations of about 0.001 to 0.01% should be employed. It preferably is present in the form of a pharmaceutically acceptable salt thereof, e.g., hydrochloride, hydrobromide, sulfate, phosphate, acetate, succinate, tartrate, benzoate, citrate, lactate or maleate, preferably the hydrochloride. Although acid addition salts of biphenamine are disclosed in U.S. Pat. No. 1,976,922 as having local anesthetic activity at a 2% concentration, neither its ability to promote healing when applied topically nor its effectiveness on the skin for any purpose at lower concentrations is suggested.

The skin penetrant generally is present in the aqueous mixture comprising the biphenamine at relatively low concentrations, e.g., at least about 1%, which concentrations lack any significant debriding activity in the absence of the biphenamine. DMSO is employed at concentrations of less than 5%, e.g., 1–5%, preferably about 2.5%. At these concentrations, DMSO exhibits neither the debriding and healing effects achieved when it is applied to the skin in admixture with biphenamine nor the side effects observed at higher concentrations, e.g., skin rash. Propylene glycol is employed at concentrations of about 1% to 90%, preferably about 5% to 15%, more preferably about 10%. Propylene glycol has desirable emollient and thickening qualities, which therefore makes it preferable in some formulations and with some patients.

Unmodified aloe vera is preferably employed full strength as the aqueous vehicle for the biphenamine. Therefore, the mixtures of this invention preferably are 99+% aloe vera. However, the aloe vera can be mixed with 10–90% by weight thereof of sterile water or isotonic saline solution. Alternatively, concentrates of the aloe vera can be used or the isolated solids thereof can be redissolved in sterile water or isotonic solution.

The biphenamine and optional skin penetrant and the aloe vera are applied topically, sequentially or preferably in admixture on successive occasions, e.g., as frequently as every hour or as infrequently as daily or longer, depending on the severity and intractibility of the pathological condition. In the case of severe burns, which produce ulcerated areas of the skin, it is desirable to apply both, preferably as a mixture, promptly after the burn occurs and on successive occasions thereafter, e.g., once every 2–12 hours for 2–14 days or until the burn is healed.

The amounts of the aqueous mixture comprising the biphenamine and the aloe vera applied to the affected area will depend on such factors as the degree of localization thereof, the concentration of biphenamine and skin penetrant therein, the individual's responsiveness to the therapy and the amounts thereof required to cover the affected area. As little as two or three drops per application of the former and 1–10 ml of the latter may be effective, whereas as much as a fluid ounce of each may be required to cover the affected area. The effectiveness of successively greater or smaller dosages can determine the optimum effective individual dose. Each can be applied to small areas with an eye dropper or a piece of cotton and to large areas as a spray or aerosol or with a surgically gloved hand.

The compositions of this invention, especially those wherein the aloe vera is the aqueous vehicle for the biphenamine, are also effective for the amelioration of the pain associated with the condition being treated. From clinical observations, when a composition of this invention is applied to the affected area promptly after a skin burn and on successive occasions thereafter, not only is pain promptly ameliorated or eliminated, the healing process is facilitated, apparently by the suppression of the inflammatory response and infection. The compositions of this invention are also useful for promoting the healing of a variety of pathological conditions of the skin, and other optically accessible areas of the body, e.g., those caused by viral, bacterial, fungal and other microorganism infections or by localized inflammatory conditions, particularly those which produce a lesion in or a pathological thickening of the epithelium, e.g., scabs, tumorous tissue, e.g., herpes virus lesions, fungus infections of the perineum, feet, hands, ear canal, inflammation or sclerosis of the ear drum, urinary bladder, urethra, abscess cavities, leg ulcers, bed sores, infected sinuses, senile keratosis, animal and insect bites.

It is postulated on the basis of studies at the cellular level that enzyme imbalances cause physiological abnormalities which are corrected according to this invention by the skin penetrant carrying the biphenamine to the situs of the abnormality. Consequently, in addition to ameliorating the pain associated with wounds and burns, the healing thereof is facilitated by the compositions of this invention by the suppression of the inflammatory response. Additionally, the biphenamine inhibits infection of the situs of the wound and debriding of dead or injured tissue.

Although biphenamine hydrochloride as a 1% ointment is known to be useful for the treatment of minor burns, minor skin irritations or insect bites and to have bactericidal, fungicidal and antihistaminic properties at that concentration, it is surprising that concentrations thereof of only about 0.1% are equally or more effective when employed as an aqueous mixture with a skin penetrant such as DMSO or propylene glycol. Although U.S. Pat. No. 2,594,350 teaches that a 0.14% solution of the mandelic acid salt of biphenamine is useful as a urinary antiseptic and germicide, the activity thereof is due in part to the known urinary bactericidal activity of mandelic acid.

Contemplated alternatives of the method of this invention are methods otherwise corresponding thereto in which instead of employing a fluid or semi-fluid gel or a paste, the biphenamine is incorporated into a solid hydrogel, e.g., as disclosed in U.S. Pat. Nos. 3,264,202; 3,419,006; 3,900,378; 3,993,551, -552 and -553; and 4,058,124 which is used as an aqueous bandage to cover the affected area during the debriding process.

The method of this invention can be employed to treat (debride) lesions associated with the following conditions:

infected or traumatic wounds; thermal, electrical, chemical and traumatic burns; scrapes, abrasions; lesions associated with herpes of the urogenital tract; herpes intercostal, herpes labialis, herpes of the tongue, herpes on the inside of the mouth or gingiva, herpes of the face, eye, nose, sinus or occiput, and herpes of any nerve route, fungal infections which produce lesions; athlete's foot which produces fissures or lesions in the skin; plantar warts; varicose ulcers; leg ulcers from impaired circulation; hemorrhoids and fissures in the colon; sunburn; oral surgery; pimples, pustules or infected areas such as splinters or other bodies; insect bites; bladder inflammations; senile keratosis; skin cancers (basal cell or squamous epithelioma); human and animal bites; adenocarcinoma corpus uteri; adenocarcinoma large bowel; and any other necrotic wound to debride, whether benign or malignant, sterile or infected with bacteria virus or fungus.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

The following are examples of compositions which can be employed in the method of this invention, which compositions are claimed in the above-cited parent application and patent.

COMPOSITIONS a. Dissolve 0.1% by weight of biphenamine hydrochloride (1 gram) in 999 grams of unmodified aloe vera (the juice from the aloe vera plant). The viscosity thereof, if desired, can be increased with any conventional viscosity enhancing agent, e.g., carboxymethylcellulose. The biphenamine can also be mixed as a 10% solution thereof in sterile water with the aloe vera in amounts to produce a 0.01–0.5%, preferably about 0.1% solution thereof in the latter.

b. A 0.1% solution of biphenamine hydrochloride in DMSO and aloe vera can be prepared by mixing 25 grams of DMSO with 975 grams of aloe vera containing 1 gram of biphenamine hydrochloride dissolved therein.

c. Dissolve 0.1% by weight of biphenamine hydrochloride (1 gram) in 999 grams of unmodified sterile isotonic water. The viscosity thereof, if desired, can be increased with any conventional viscosity enhancing agent, e.g., carboxymethylcellulose. The biphenamine can also be mixed as 10% solution thereof in sterile water with the sterile isotonic water in amounts to produce a 0.01–0.5%, preferably about 0.1% solution thereof in the latter.

COMPOSITION 2 a. A lotion can be formulated in the conventional manner from the following ingredients, after dissolving the biphenamine hydrochloride and buffer in the water.

| Biphenamine.HCl | 1 gm |
| Cetyl alcohol | 200 gm |
| Propylene glycol | 100 gm |
| Sodium lauryl sulfate | 15 gm |
| Aloe vera q.s. | 1000 cc | b. The above lotion can also be prepared with 50 cc of DMSO included therein.

COMPOSITION 3 a. An ointment can be produced from the following ingredients, after dissolution of the biphenamine hydrochloride in water.

| Biphenamine.HCl | 1 gm |
| Glyceryl monostearate Acid Type | 180 gm |
| Stearyl alcohol | 50 gm |
| Polysorbate 80 | 20 gm |
| Aloe vera q.s. | 1,000 cc | b. An ointment can also be prepared in which 50 cc of aloe vera is replaced by 50 grams of DMSO or propylene glycol.

COMPOSITION 4 a. An aqueous alcoholic ointment can be prepared by blending the following ingredients, with the biphenamine hydrochloride first dissolved in the water.

| Biphenamine.HCl | 100 mg |
| Ethanol | 10 gm |
| Corbowax 1,500 | 20 gm |
| Aloe vera q.s. | 1,000 | b. An ointment in which the 5 cc of aloe vera is replaced by 10 gm of DMSO or propylene glycol can similarly be prepared.

COMPOSITION 5 a. Suppositories can be cast from a melt of the following ingredients, after first dissolving the biphenamine hydrochloride in the water.

| Biphenamine.HCl | 70 mg |
| Sodium stearate | 10 gm |
| Glycerin | 45 gm |
| Aloe vera | 10 gm | b. Suppositories in which the 3.4 gm of aloe vera is replaced by 3.4 gm of DMSO or propylene glycol can also be produced.

EXAMPLE

A geriatric patient with old burns (several years) on his legs which did not heal, required surgical debriding of necrotic skin with "betadine" to suppress infection. The treatment was associated with considerable pain and discomfort. He attempted to self-treat the condition with aloe vera, but without success. However, when a 0.1% solution of biphenamine HCl dissolved in water was applied to the affected area to debride the necrotic tissue, followed by application of aloe vera to reduce inflammation, pain and irritation, a significant improvement in the condition was noted. However, even faster and more complete healing was accomplished without accompanying granulation by applying the biphenamine HCl as a 0.1% solution in the aloe vera to the affected area several times daily on successive days (about 2 weeks).

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A method for promoting the healing of an abnormal, ulcerated necrotic tissue or skin mucous membrane of a patient which comprises applying topically to the affected area of the patient an amount of biphenamine, as an aqueous mixture comprising a pharmaceutically acceptable carrier, effective to promote debridement of necrotic tissue from the affected area, thereby promoting the healing of the affected area, and also applying topically to the affected area sequentially or in admixture therewith an amount of the juice of the aloe vera plant effective to further promote wound healing.

2. A method according to claim 1, wherein the affected area is on the skin.

3. A method according to claim 2, wherein the mixture is applied to the affected area on successive occasions.

4. A method according to claim 1, wherein the biphenamine is applied to the affected area in admixture with the aloe vera.

5. A method according to claim 4, wherein the biphenamine is applied as a solution in the aloe vera.

6. A method according to claim 5, wherein the biphenamine is applied as a solution of the hydrochloride salt thereof in the aloe vera at a concentration of about 0.1% to 1%.

7. A method according to claim 6, wherein the mixture is applied to the affected area at least once a day on a plurality of successive days.

8. A method according to claim 6, wherein the affected area is the skin and the biphenamine hydrochloride is present in the aloe vera at a concentration of about 0.1%.

9. A method according to claim 8, wherein the mixture is applied to the affected area at least once a day on a plurality of successive days.

10. A composition adapted for application to the skin consisting essentially of an about 0.1 to 1.0% solution of biphenamine in aloe vera.

11. A composition according to claim 10, wherein the biphenamine is present therein as an about 0.1% solution of the hydrochloride thereof.

* * * * *

UNITED STATES PATENT AND TRADEMARK OFFICE
CERTIFICATE OF CORRECTION

PATENT NO. : 4,708,873

DATED : November 24, 1987

INVENTOR(S) : Thomas L. Schulte

It is certified that error appears in the above-identified patent and that said Letters Patent is hereby corrected as shown below:

The term of this patent subsequent to February 5, 2002 has been disclaimed.

Signed and Sealed this

Sixteenth Day of February, 1988

Attest:

*Attesting Officer*

DONALD J. QUIGG

*Commissioner of Patents and Trademarks*